US012611423B2

(12) United States Patent
Degling-Wikingsson et al.

(10) Patent No.: US 12,611,423 B2
(45) **Date of Patent: *Apr. 28, 2026**

(54) MEDICAL USE OF TAFOXIPARIN

(71) Applicant: DILAFOR AB, Solna (SE)

(72) Inventors: Lena Degling-Wikingsson, Spånga (SE); Gunvor Ekman-Ordeberg, Danderyd (SE)

(73) Assignee: DILAFOR AB, Solna (SE)

( * ) Notice: Subject to any disclaimer, the term of this patent is extended or adjusted under 35 U.S.C. 154(b) by 202 days.

This patent is subject to a terminal disclaimer.

(21) Appl. No.: 18/142,121

(22) Filed: May 2, 2023

(65) Prior Publication Data

US 2023/0355658 A1 Nov. 9, 2023

(30) Foreign Application Priority Data

May 3, 2022 (EP) .................................... 22171313
Mar. 28, 2023 (EP) .................................... 23164674

(51) Int. Cl.

| | |
|---|---|
| ***A61K 31/737*** | (2006.01) |
| ***A61K 9/00*** | (2006.01) |
| ***A61K 31/727*** | (2006.01) |
| ***A61P 15/04*** | (2006.01) |

(52) U.S. Cl.

CPC .......... *A61K 31/737* (2013.01); *A61K 9/0019* (2013.01); *A61K 31/727* (2013.01); *A61P 15/04* (2018.01)

(58) Field of Classification Search

CPC .............................. A61K 31/737; A61P 15/04
See application file for complete search history.

(56) References Cited

U.S. PATENT DOCUMENTS

2015/0057226 A1* 2/2015 Ekman-Ordeberg ........................ A61K 31/727 514/11.6
2025/0177435 A1 6/2025 Degling-Wikingsson et al.

FOREIGN PATENT DOCUMENTS

| | | | |
|---|---|---|---|
| WO | 2003/055499 | A1 | 7/2003 |
| WO | 2013/095279 | A1 | 6/2013 |
| WO | 2013/147689 | A1 | 10/2013 |
| WO | 2013/147690 | A1 | 10/2013 |
| WO | 2013/169194 | A1 | 11/2013 |
| WO | 2014/202982 | A1 | 12/2014 |
| WO | 2021/165240 | A1 | 8/2021 |

OTHER PUBLICATIONS

Roos et al., Prostaglandin Receptors in the Human Cervix at Term and Postterm Pregnancy. Reproductive Sciences. Mar. 2011;18(4):315A, poster S-071.
Akerud, Uterine Remodeling During Pregnancy, Studies on the Effect of Heparin/Heparan Sulfate. Department of Experimental Medical Science, Lund University. 120 pages, (2009).
Beers et al., Abnormalities and Complications of Labor and Delivery. The Merck Manual of Diagnosis and Therapy, Seventeenth Edition. Chapter 253, pp. 2062-2067, (1999).
Ekman-Ordeberg et al., Does low molecular weight heparin shorten term labor? Acta Obstet Gynecol Scand. 2010;89(1):147-50.
Ekman-Ordeberg et al., Low molecular weight heparin stimulates myometrial contractility and cervical remodeling in vitro. Acta Obstet Gynecol Scand. 2009;88(9):984-9.
Ekman-Ordeberg et al., Tafoxiparin a new drug counteracting labor arrest by inccreased myometrial contractility and enhanced cervical cytokine synthesis. Karolinska Institutet. 1 page, (2011).
Ekman-Ordeberg et al., Tafoxiparin, a novel drug candidate for cervical ripening and labor augmentation: results from 2 randomized, placebo-controlled studies. AJOG. Am J Obstet Gynecol. 10 pages, (2022). Pre-publication edition.
Ekman-Ordeberg, Tafoxiparin a New Drug Candidate (Phase IIb) for Cervical and Uterine Priming at Planned Delivery. Reproductive Sciences. Mar. 2022;29(Suppl 1):70A, Abstract O-063.
Ekman-Ordeberg, Tafoxiparin, a New Drug Candidate: A Scientific Journey Clarifying the ECM Remodeling Process in Labor and the Transition of Knowledge into Late Stage Clinical Development. Reproductive Sciences. Mar. 2000;27(Suppl 1):219A, Abstract F-045.
Faltin-Traub et al., Reliability of the Bishop score before labour induction at term. Eur J Obstet Gynecol Reprod Biol. Feb. 10, 2004;112(2):178-81.
Isma et al., The effect of low molecular weight heparin (dalteparin) on duration and initiation of labour. J Thromb Thrombolysis. Aug. 2010;30(2):149-53.
Karolinska Development, Invitation to subscribe for shares in Karolinska Development AB (publ). pp. 45-46, (2011).
Mackenzie, Induction of labour at the start of the new millennium. Reproduction. Jun. 2006;131(6):989-98.
Nielsen et al., The distribution and predictive value of Bishop scores in nulliparas between 37 and 42 weeks gestation. J Matern Fetal Neonatal Med. Mar. 2012;25(3):281-5.
Penfield et al., Labor Induction Techniques: Which Is the Best? Obstet Gynecol Clin North Am. Dec. 2017;44(4):567-582.
Rey et al., Dalteparin for the prevention of recurrence of placental-mediated complications of pregnancy in women without thrombophilia: a pilot randomized controlled trial. J Thromb Haemost. Jan. 2009;7(1):58-64.

(Continued)

*Primary Examiner* — Layla D Berry
(74) *Attorney, Agent, or Firm* — McCarter & English, LLP; Steven G. Davis; James M. Alburger

(57) ABSTRACT

The present invention is directed to tafoxiparin for use in the spontaneous onset of labor in a term pregnant woman, wherein tafoxiparin is administered in a daily dose of 30-320 mg per day.

22 Claims, 6 Drawing Sheets

(56) References Cited

OTHER PUBLICATIONS

Teixeira et al., The Bishop Score as a determinant of labour induction success: a systematic review and meta-analysis. Arch Gynecol Obstet. Sep. 2012;286(3):739-53.
Ekman-Ordeberg, Tafoxiparin, a New Drug Candidate: A Scientific Journey Clarifying the ECM Remodeling Process in Labor and the Transition of Knowledge into Late Stage Clinical Development. Reproductive Sciences. Mar. 2020;27(Suppl 1):219A, Abstract F-045.
Fryar et al., Mean Body Weight, Height, Waist Circumference, and Body Mass Index Among Adults: United STates, 1999-2000 Through 2015-2016. National Health Statistics Report. Dec. 20, 2018;122:1-16.
International Search Report and Written Opinion for Application No. PCT/EP2023/061494, dated Jul. 13, 2023, 10 pages.
International Preliminary Report on Patentability for Application No. PCT/EP2023/061494, dated Nov. 14, 2024, 8 pages.

* cited by examiner

MEDICAL USE OF TAFOXIPARIN

CROSS-REFERENCE TO RELATED APPLICATIONS

This application claims the benefit of European Patent Application No. 22 171 313.4, filed on May 3, 2022 and European Patent Application No. 23 164 674.6, filed on Mar. 28, 2023, the entire contents of which are incorporated herein by reference.

FIELD OF THE INVENTION

The present invention is directed to the heparin derivative tafoxiparin for use in the spontaneous onset of labor in a term pregnant woman.

BACKGROUND OF THE INVENTION

During pregnancy, the uterus is mainly held in a quiescent state with a stiff and closed cervix, designed to maintain the fetus inside the womb during gestation. Slowly during pregnancy and more rapidly closer to term, the uterine tissue undergoes structural changes of the extracellular matrix (ECM) and increase in gap junctions facilitating the onset and progress of labor. Concomitantly, remodeling of the cervix to a more softened state occurs, a process generally referred to as cervical ripening. This ripening process is essential for the induction of the latent stage of labor and dysregulations in this process may result in an inability for the natural labor process to be spontaneously initiated in due time. Failure of spontaneous onset of the labor process may lead to complications for both the mother and the unborn child. This is especially true for nulliparous women, i.e. women who have never given birth previously.

Standard methods used for inducing labor are directed towards amniotomy, pharmaceutical intervention or a combination of both. The choice of which intervention to use is mainly based on the ripeness of the cervix. If the cervix is considered ripe, mechanical stimulation alone or combined with intravenous infusion of oxytocin may be enough to initiate labor within a short time span, but in cases where the cervix is unfavorable, pharmacologic intervention in the form of a prostaglandin such as PGE2 or PGE1, or cervical balloon may be required (Penfield C A et al 2017*; Obstet Gynecol Clin N Ann* 44; pp. 567-582).

The use of prostaglandins E2 (PGE2) and E1 (PGE1) administered locally has been routine for many years. However, due to side effects with hypercontractility with bad influence on the umbilical blood flow with threatening asphyxia, a lower dose of per oral PGE1 has been tested (Penfield C A et al 2017*; Obstet Gynecol Clin N Ann* 44; pp. 567-582).

Oxytocin, an endogenous mediator of labor, is a potent inducer of uterine contractions. Administration of exogenous oxytocin intravenously is commonly used to induce labor, especially when used in combination with amniotomy (Mackenzie I. Z. 2006*; Reproduction;* 131(6); pp. 989-998).

WO 2003/055499 describes the use of certain sulfated glycosaminoglycans for the prevention and treatment of slow progress of term labor. WO 2013/147689 describes the use of a chemically modified heparin or heparan sulfate in labor induction. WO 2013/147690 describes the use of a chemically modified heparin or heparan sulfate in labor arrest. WO 2013/169194 describes the use of a chemically modified heparin or heparan sulfate in the treatment of post partum hemorrhage (PPH). WO 2013/095279 describes a novel chemically modified glycosaminoglycan which is described as useful for the prevention and treatment of protracted labor (dystocia), protein leakage such as Gorham Stout syndrome, sepsis and protein-losing enteropathy. WO 2014/202982 describes a novel manufacturing process for the preparation of a chemically modified glycosaminoglycan. WO 2021/165240 describes the use of tafoxiparin in the treatment of preeclampsia. The Abstract no. 0-063 in Reproductive Sciences Vol. 29, Supplement 1, March 2022 mentions a study examining the effect on cervical ripening rate by using tafoxiparin for up to seven days.

DESCRIPTION OF THE INVENTION

An object of the invention is a novel therapy for achieving a spontaneous onset of labor in a term pregnant woman.

More particularly the invention is directed to tafoxiparin for use in the spontaneous onset of labor in a term pregnant woman, wherein said tafoxiparin is administered in a daily dose of 30-320 mg.

Still an aspect of the invention is the use of tafoxiparin as monotherapy.

DETAILED DESCRIPTION OF THE INVENTION

Figure 1:
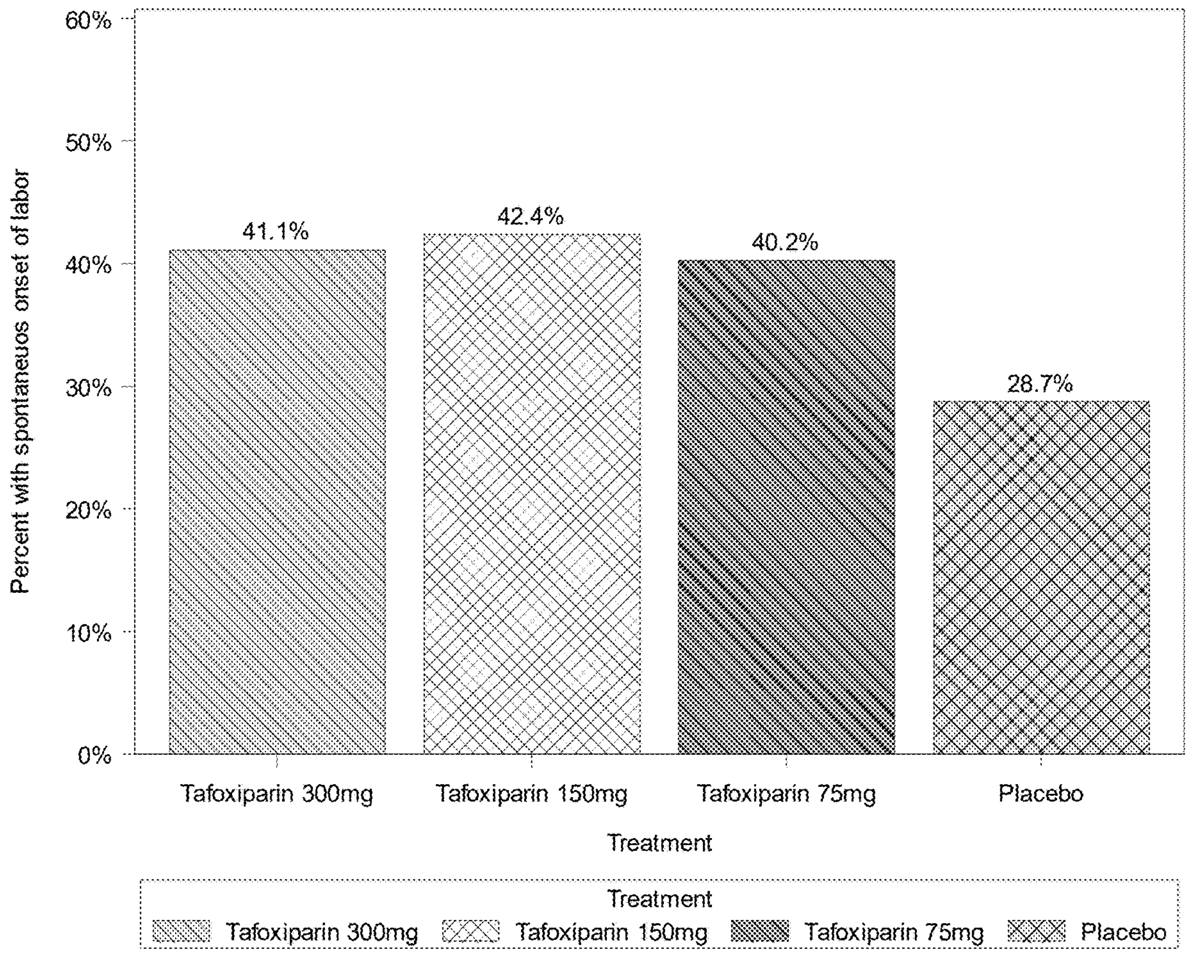
FIG. 1 shows the proportion of women achieving a spontaneous onset of labor when treated with 300 mg tafoxiparin, 150 mg tafoxiparin, 75 mg tafoxiparin, and placebo, respectively.

An aspect of the invention is tafoxiparin (i) having an antifactor IIa activity of less than 10 IU/mg;

(ii) having an antifactor Xa activity of less than 10 IU/mg; and (iii) having a weight average molecular weight (Mw) from 4.6 to 6.9 kDa;

(iv) having a predominantly occurring saccharide of (Formula I):

Formula (I)

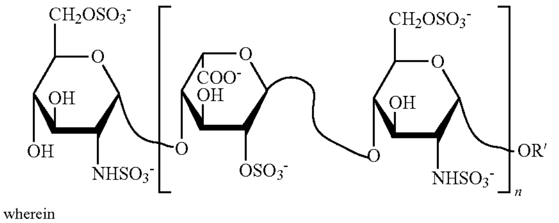

wherein

R' = 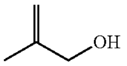 or 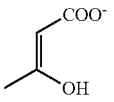

n is an integer from 2 to 20, so that the polysaccharide chains have from 2 to 20 disaccharide units corresponding to molecular weights between 1.2 and 12 kDa;

(v) wherein the polysaccharide chains are essentially free of chemically intact non-sulfated iduronic and/or glucuronic acids from the pentasaccharide sequences mediating the anticoagulant effect; and (vi) wherein the chemically modified glycosaminoglycans have a distribution of polysaccharides and their corresponding molecular weight expressed as cumulative % of weight according to the table:

| Molecular mass [kDa] | Cumulative weight [%] |
|---|---|
| >10 | 4-15 |
| >8 | 10-25 |
| >6 | 22-45 |
| >3 | >70 |

for use in the spontaneous onset of labor in a term pregnant woman, wherein said tafoxiparin is administered in a daily dose of 30-320 mg per day.

Yet an aspect of the invention is tafoxiparin for use in the spontaneous onset of labor in a term pregnant woman, wherein said tafoxiparin is administered as monotherapy in a daily dose of 30-320 mg per day.

In one aspect of the invention, the predominantly occurring polysaccharide chains in tafoxiparin as used in accordance with the invention, have between 6 and 12 disaccharide units with molecular weights from 3.6-7.2 kDa.

In yet an aspect of the invention, tafoxiparin as described herein produces signals at 5.95 ppm and 6.15 ppm in an 1H-NMR spectrum.

In one aspect of the invention, tafoxiparin as used in accordance with the invention, comprises non-reducing end unsaturated glucosamines presented as signals in the interval of 5.0 to 6.5 ppm in a 1H-NMR spectrum with an intensity (% ratio) of less than 4% in relation to the signal at 5.42 ppm from native heparin.

One aspect of the invention is tafoxiparin as herein described, for use as monotherapy.

An aspect of the invention is a method for the spontaneous onset of labor in a term pregnant woman, whereby a therapeutically effective amount of tafoxiparin:

(i) having an antifactor IIa activity of less than 10 IU/mg;

(ii) having an antifactor Xa activity of less than 10 IU/mg; and (iii) having a weight average molecular weight (Mw) from 4.6 to 6.9 kDa;

(iv) having a predominantly occurring saccharide of (Formula I):

Formula (I)

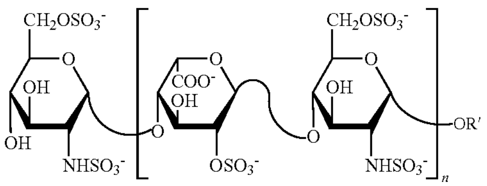

wherein

R'= 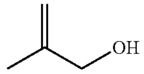 or 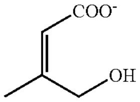

n is an integer from 2 to 20, so that the polysaccharide chains have from 2 to 20 disaccharide units corresponding to molecular weights between 1.2 and 12 kDa;

(v) wherein the polysaccharide chains are essentially free of chemically intact non-sulfated iduronic and/or glucuronic acids from the pentasaccharide sequences mediating the anticoagulant effect; and (vi) wherein the chemically modified glycosaminoglycans have a distribution of polysaccharides and their corresponding molecular weight expressed as cumulative % of weight according to the table:

| Molecular mass [kDa] | Cumulative weight [%] |
|---|---|
| >10 | 4-15 |
| >8 | 10-25 |
| >6 | 22-45 |
| >3 | >70 |

is administered in a daily dose of 30-320 mg to said term pregnant woman.

Yet an aspect of the invention is a method for the spontaneous onset of labor in a term pregnant woman, whereby a therapeutically effective amount of tafoxiparin is administered to said term pregnant woman as monotherapy.

An aspect of the invention is the use of tafoxiparin:

(i) having an antifactor IIa activity of less than 10 IU/mg;

(ii) having an antifactor Xa activity of less than 10 IU/mg; and (iii) having a weight average molecular weight (Mw) from 4.6 to 6.9 kDa;

(iv) having a predominantly occurring saccharide of (Formula I):

Formula (I)

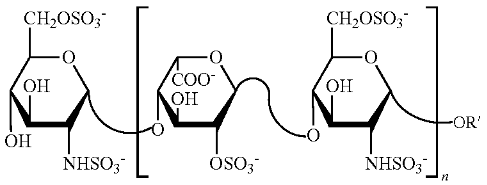

wherein

-continued

R'= 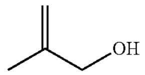 or 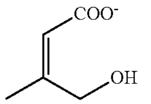

n is an integer from 2 to 20, so that the polysaccharide chains have from 2 to 20 disaccharide units corresponding to molecular weights between 1.2 and 12 kDa;

(v) wherein the polysaccharide chains are essentially free of chemically intact non-sulfated iduronic and/or glucuronic acids from the pentasaccharide sequences mediating the anticoagulant effect; and (vi) wherein the chemically modified glycosaminoglycans have a distribution of polysaccharides and their corresponding molecular weight expressed as cumulative % of weight according to the table:

| Molecular mass [kDa] | Cumulative weight [%] |
|---|---|
| >10 | 4-15 |
| >8 | 10-25 |
| >6 | 22-45 |
| >3 | >70 |

for the manufacture of a medicament for use in a daily dose of 30-320 mg in the spontaneous onset of labor in a term pregnant woman.

In one aspect of the invention, tafoxiparin is for use as monotherapy.

In one aspect of the invention, the daily dose of tafoxiparin as used according to the invention, is 50-320 mg.

In one aspect of the invention, the daily dose of tafoxiparin as used according to the invention, is 50-300 mg.

In yet an aspect of the invention, the daily dose of tafoxiparin as used according to the invention is 75-320 mg.

In yet an aspect of the invention, the daily dose of tafoxiparin as used according to the invention is 75-300 mg.

In yet an aspect of the invention, the daily dose of tafoxiparin as used according to the invention is 75-150 mg.

Yet an aspect of the invention is tafoxiparin for use in the spontaneous onset of labor in a term pregnant woman, wherein said tafoxiparin is administered in a daily dose of 50-320 mg, such as 50-300 mg.

Yet an aspect of the invention is tafoxiparin for use in the spontaneous onset of labor in a term pregnant woman, wherein said tafoxiparin is administered in a daily dose of 75-320 mg, such as 75-300 mg.

Yet an aspect of the invention is tafoxiparin for use in the spontaneous onset of labor in a term pregnant woman, wherein said tafoxiparin is administered in a daily dose of 75-150 mg.

Yet an aspect of the invention is tafoxiparin for use in the spontaneous onset of labor in a term pregnant woman, wherein said tafoxiparin is administered as monotherapy in a daily dose of 50-320 mg, such as 50-300 mg.

Yet an aspect of the invention is tafoxiparin for use in the spontaneous onset of labor in a term pregnant woman, wherein said tafoxiparin is administered as monotherapy in a daily dose of 75-320 mg, such as 75-300 mg.

Yet an aspect of the invention is tafoxiparin for use in the spontaneous onset of labor in a term pregnant woman, wherein said tafoxiparin is administered as monotherapy in a daily dose of 75-150 mg.

In one aspect of the invention, the daily dose of tafoxiparin as used in accordance with the invention is 30 mg per day; or 40 mg per day; or 50 mg per day; or 60 mg per day; or 70 mg per day; or 80 mg per day; or 90 mg per day; or 100 mg per day; or 110 mg per day; or 120 mg per day; or 130 mg per day; or 140 mg per day; or 150 mg per day; or 160 mg per day; or 170 mg per day; or 180 mg per day; or 190 mg per day; or 200 mg per day; or 210 mg per day; or 220 mg per day; or 230 mg per day; or 240 mg per day; or 250 mg per day; or 260 mg per day; or 270 mg per day; or 280 mg per day; or 290 mg per day; or 300 mg per day; or 310 mg per day; or 320 mg per day.

In one aspect of the invention, the daily dose of tafoxiparin as used in accordance with the invention is selected from any one daily dose of 30-320 mg, such as 35-320 mg; 40-320 mg, such as 45-320 mg; 50-320 mg, such as 55-320 mg; 60-320 mg, such as 65-320 mg; 70-320 mg, such as 75-320 mg; 80-320 mg, such as 85-320 mg; 90-320 mg, such as 95-320 mg; 100-320 mg, such as 105-320 mg; 110-320 mg, such as 115-320 mg; 120-320 mg, such as 125-320 mg; 130-320 mg, such as 135-320 mg; 140-320 mg, such as 145-320 mg; 150-320 mg, such as 155-320 mg; 160-320 mg, such as 165-320 mg; 170 to 320 mg, such as 175-320 mg; 180-320 mg, such as 185-320 mg; 190-320 mg, such as 195-320 mg; 200-320 mg, such as 205-320 mg; 210-320 mg, such as 215-320 mg; 220-320 mg, such as 225-320 mg; 230-320 mg, such as 235-320 mg; 240-320 mg such as 245-320 mg; 250-320 mg, such as 255-320 mg; 260-320 mg, such as 265-320 mg; 270-320 mg, such as 275-320 mg; 280-320 mg, such as 285-320 mg; and 290-320 mg, such as 295-320 mg; 300-320 mg, such as 305-320 mg; and 310-320 mg, such as 315-320 mg.

In one aspect of the invention, tafoxiparin and the use as herein described, is for use once daily.

In yet an aspect of the invention, tafoxiparin and the use as herein described, is for use twice daily.

In yet an aspect of the invention, tafoxiparin and the use as herein described, is for use three times a day.

In one aspect of the invention, tafoxiparin and the use as herein described, is for use up to 14 days (day 14 inclusive).

In one aspect of the invention, tafoxiparin and the use as herein described, is for use for 1 day, or 2 days, or 3 days, or 4 days, or 5 days, or 6 days, or 7 days, or 8 days, or 9 days, or 10 days, or 11 days, or 12 days, or 13 days, or 14 days.

One aspect of the invention is tafoxiparin for use in the spontaneous onset of labor in a term pregnant woman, wherein the daily dose 30-320 mg of tafoxiparin is administered as a double dose (i.e. 60-640 mg per day).

In yet an aspect of the invention, tafoxiparin is for use in the spontaneous onset of labor in a term pregnant woman, wherein said subject (woman) is an obese subject (woman). The wording obese means a subject (woman) who has a BMI (body mass index) of 30 or higher, such as 35 or higher, or 40 or higher, or 45 or higher, or 50 or higher.

In one aspect of the invention, tafoxiparin and the use as herein described, is in a term pregnant woman in gestation week 36-42.

In one aspect of the invention, tafoxiparin and the use as herein described, is in a term pregnant woman in gestation week 37-42. In yet an aspect of the invention, tafoxiparin and the use as herein described, is in a term pregnant woman in gestation week 38-42. In yet an aspect of the invention, tafoxiparin and the use as herein described, is in a term pregnant woman in gestation week 39-42. In yet an aspect of the invention, tafoxiparin and the use as herein described, is in a term pregnant woman in gestation week 40-42. In yet an aspect of the invention, tafoxiparin and the use as herein described, is in a term pregnant woman in gestation week 41-42. In yet an aspect of the invention, tafoxiparin and the use as herein described, is in a term pregnant woman in gestation week 42.

In one aspect of the invention, tafoxiparin and the use as herein described, is in a term pregnant woman having an unripe cervix.

In one aspect of the invention, the term pregnant woman has a Bishop score of 6 or less.

In one aspect of the invention, the term pregnant woman has a Bishop score of 5 or less.

In one aspect of the invention, the term pregnant woman has a Bishop score of 4 or less.

In one aspect of the invention, the term pregnant woman has a Bishop score of 3 or less.

In one aspect of the invention, the term pregnant woman has a Bishop score of 2 or less.

In one aspect of the invention, the term pregnant woman has a Bishop score of 1 or less.

In one aspect of the invention, the term pregnant woman has a Bishop score of 0.

An aspect of the invention is tafoxiparin for use in the spontaneous onset of labor in a term pregnant woman who is nulliparous, wherein the tafoxiparin is administered to said woman in a daily dose of 30-320 mg.

An aspect of the invention is tafoxiparin for use in the spontaneous onset of labor in a term pregnant woman who is nulliparous, wherein the tafoxiparin is administered as monotherapy to said woman in a daily dose of 30-320 mg.

An aspect of the invention is tafoxiparin for use in the spontaneous onset of labor in a term pregnant woman who is nulliparous and having a Bishop score of 6 or less, wherein the tafoxiparin is administered to said woman in a daily dose of 30-320 mg.

An aspect of the invention is tafoxiparin for use in the spontaneous onset of labor in a term pregnant woman who is nulliparous and having a Bishop score of 6 or less, wherein the tafoxiparin is administered as monotherapy to said woman in a daily dose of 30-320 mg.

In one aspect of the invention, tafoxiparin is for use in a term pregnant woman who has given birth earlier, or who has not given birth earlier (nulliparous).

In one aspect of the invention, tafoxiparin is for use in labor priming of a term pregnant woman, as described herein.

In one aspect of the invention, tafoxiparin is for use in priming a term pregnant woman to achieve a spontaneous onset of labor, as described herein.

One aspect of the invention is tafoxiparin for use to facilitate for a term pregnant woman to achieve a spontaneous onset of labor, as described herein.

Yet an aspect of the invention is tafoxiparin for use to support a term pregnant woman to achieve a spontaneous onset of labor, as described herein.

Yet an aspect of the invention is tafoxiparin for use to initiate a spontaneous onset of labor in a term pregnant woman, as described herein.

Yet an aspect of the invention is tafoxiparin for use to remodel the cervix and the myometrium of a term pregnant woman to achieve a spontaneous onset of labor, as described herein.

In one aspect of the invention, tafoxiparin for use as described throughout the patent specification, comprises cervical ripening.

An aspect of the invention is tafoxiparin for use in cervical ripening in a term pregnant woman, wherein the tafoxiparin is administered to said woman in a daily dose of 30-320 mg.

An aspect of the invention is tafoxiparin for use in cervical ripening in a term pregnant woman, wherein the tafoxiparin is administered as monotherapy to said woman in a daily dose of 30-320 mg.

An aspect of the invention is tafoxiparin for use in cervical ripening in a term pregnant woman having a Bishop score of 6 or less, wherein the tafoxiparin is administered as monotherapy to said woman in a daily dose of 30-320 mg.

An aspect of the invention is tafoxiparin for use in cervical ripening in a term pregnant woman who is nulliparous and has a Bishop score of 6 or less, wherein the tafoxiparin is administered to said woman in a daily dose of 30-320 mg.

An aspect of the invention is tafoxiparin for use in cervical ripening in a term pregnant woman who is nulliparous and has a Bishop score of 6 or less, wherein the tafoxiparin is administered as monotherapy to said woman in a daily dose of 30-320 mg.

An aspect of the invention is tafoxiparin for use in the reduction of fetal distress of the fetus of a term pregnant woman.

An aspect of the invention is tafoxiparin for use as described throughout the patent specification, further providing an increase in the rate of vaginal delivery. The wording "increase in vaginal delivery" means that treatment with tafoxiparin as herein described, reduces the need for instrumental delivery.

An aspect of the invention is tafoxiparin for use as described throughout the patent specification, for providing a reduction of the need for instrumental delivery. The wording "providing a reduction of the need for instrumental delivery" means that the need for instrumental delivery is less frequent in women who have been treated with tafoxiparin compared to the need for instrumental delivery needed in women who have not been treated with tafoxiparin.

One aspect of the invention is tafoxiparin for use in a term pregnant woman who has an unfavorable cervix.

Yet an aspect of the invention is tafoxiparin for use in a term pregnant woman for triggering spontaneous onset of labor.

One aspect of the invention is tafoxiparin for use in a term pregnant woman who has an unfavorable cervix and wherein said woman is subjected to a triggering therapy with tafoxiparin for achieving onset of labor.

One aspect of the invention is tafoxiparin for use as a triggering therapy in a term pregnant woman who has an unfavorable cervix, for reducing the need for Standard of Care (SOC) intervention in order to achieve onset of labor.

DEFINITIONS

Tafoxiparin is a heparin derivative with the company compound code DF01. The INN (International Nonproprietary Name) for DF01 is tafoxiparin sodium. The CAS registry number (CAS RN) for tafoxiparin is RN 1638190-65-4. DF01 is a depolymerized form of heparin with essentially no anticoagulant activity.

More specifically, tafoxiparin is a heparin derivative:

(i) having an antifactor IIa activity of less than 10 IU/mg;

(ii) having an antifactor Xa activity of less than 10 IU/mg; and (iii) having a weight average molecular weight (Mw) from 4.6 to 6.9 kDa, such as 5.0-6.9 kDa;

(iv) having a predominantly occurring saccharide of (Formula I):

Formula (I)

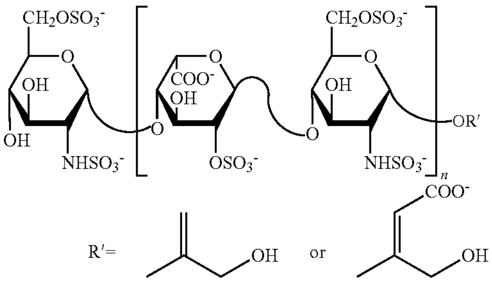

wherein n is an integer from 2 to 20, so that the polysaccharide chains have from 2 to 20 disaccharide units corresponding to molecular weights between 1.2 and 12 kDa;

(v) wherein the polysaccharide chains are essentially free of chemically intact non-sulfated iduronic and/or glucuronic acids from the pentasaccharide sequences mediating the anticoagulant effect; and (vi) wherein the chemically modified glycosaminoglycans have a distribution of polysaccharides and their corresponding molecular weight expressed as cumulative % of weight according to the table:

| Molecular mass [kDa] | Cumulative weight [%] |
|---|---|
| >10 | 4-15 |
| >8 | 10-25 |
| >6 | 22-45 |
| >3 | >70 |

The predominantly occurring polysaccharide chains of tafoxiparin have between 6 and 12 disaccharide units with molecular weights from 3.6-7.2 kDa.

Tafoxiparin may have non-reducing end unsaturated glucosamines presented as signals in the interval of 5.0 to 6.5 ppm in a 1H-NMR spectrum with an intensity (% ratio) of less than 4% in relation to the signal at 5.42 ppm from native heparin, and may also be producing signals at 5.95 ppm and 6.15 ppm in an 1H-NMR spectrum.

Tafoxiparin may comprise glycol-split residues according to the chemical structure:

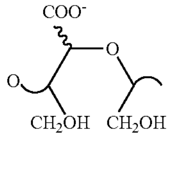

The wording spontaneous onset of labor as used herein means labor which is initiated without any further standard of care (SOC) intervention such as amniotomy, the use of balloon catheters, or use of pharmaceutical intervention, or any combination of these.

The wording labor induction as used herein, also known as inducing labor, means both ripening of the cervix and stimulation of the myometrium to obtain established labor. As used throughout the patent specification, labor induction or the wording induced into labor, means that a term pregnant woman does not achieve onset of labor without the use of standard of care therapy.

The wording spontaneous onset of labor in combination with SOC intervention as used herein means labor which is achieved in a term pregnant woman by treatment with tafoxiparin monotherapy, such as for a maximum of 7 days as herein described, and wherein said tafoxiparin monotherapy is then combined with SOC therapy.

The wording IMP (Investigational Medical product) as used herein means tafoxiparin.

The wording LMWH means low molecular weight heparin.

Standard of care (SOC) therapy as used herein means the use of amniotomy, balloon catheters, or pharmaceutical intervention, or any combination of these.

Oxytocin is a well-known pharmaceutical (a peptide hormone) for use as Standard of Care therapy to induce or increase myometrial contractions.

Prostaglandins such as PGE2 or PGE1, are well-known pharmaceuticals for use as Standard of Care to promote cervical ripening and myometrial contractions in a woman with an unripe cervix. Examples of prostaglandins commonly used in labor induction are misoprostol (PGE1) and/or dinoprostone (PGE2).

Intervention for labor induction means that standard methods are used for inducing labor. Such standard methods are amniotomy, pharmaceutical intervention or a combination of both. The choice of which intervention to use is mainly based on the ripeness of the cervix. If the cervix is considered ripe, mechanical stimulation alone or combined with intravenous infusion of oxytocin may be enough to initiate labor within a short time span, but in cases where the cervix is unfavorable, pharmacologic intervention in the form of a prostaglandin such as PGE2 or PGE1, or cervical balloon, may be required.

Balloon catheter(s) is a device used for cervical ripening to help dilate the cervix.

Amniotomy, also known as Artificial rupture of membranes (AROM) or "breaking the sac", is the intentional rupture of the amniotic sac by an obstetrical provider.

The wording pharmaceutical intervention as used throughout the patent specification means a pharmaceutical which is used as Standard of Care therapy in the induction of labor.

The wording priming a woman into labor as used herein means that tafoxiparin is administered to a term pregnant woman in order to provide a spontaneous onset of labor in said woman, or to facilitate the delivery process of the baby.

The wording triggering therapy for achieving onset of labor as used herein means that tafoxiparin is administered to a term pregnant woman in order to provide a spontaneous onset of labor in said woman, or to facilitate the delivery process of the baby.

A woman with an unripe cervix is a woman who has an inability for a natural labor process to be spontaneously initiated. A woman with an unripe cervix usually has a Bishop score of 6 or less, 5 or less, 4 or less, 3 or less, 2 or less, 1 or less, or 0.

Bishop score is a rating of the cervix's readiness to vaginally deliver a baby. Bishop score is also known as cervix score, and is a pre-labor scoring system to assist the physician in predicting whether induction of labor will be required. A Bishop score of 8 or greater is in the field of obstetrics considered to be favorable for spontaneous vaginal delivery without the requirement for induction into labor.

A Bishop score of 6 or less may be considered to be an unfavorable cervix, and which likely will require induction into labor.

Cervical ripening is a remodeling process resulting in a softening of the cervix. The cervical ripening process is judged by estimating the Bishop score changes.

Cervical dilation refers to how many centimeters the cervix of a woman has opened. During a vaginal delivery, the cervix needs to be about 10 centimeters dilated before the woman can start pushing.

Onset of labor as used herein is defined as last record of 4 cm cervical dilatation visualized in the partogram and progress of labor.

The wording monotherapy as used herein, means treatment of a term pregnant woman with tafoxiparin only.

The wording term pregnant woman as used herein is a woman who is 36 weeks pregnant or more, such as 37 weeks pregnant, or 38 weeks pregnant, or 39 weeks pregnant, or 40 weeks pregnant, or 41 weeks pregnant, or 42 weeks pregnant.

The wording post term pregnant or post term pregnancy means a pregnant woman who is post 42 weeks pregnant.

The wording nulliparous woman means a pregnant woman who has not previously been pregnant, or a woman who has not previously given birth.

The wording fetal distress is defined as abnormal cardiotocography and/or acidosis in fetal scalp blood. The fetus usually reacts at the onset of asphyxia with a series of responses, primarily a complexly regulated redistribution of blood flow that serves to limit the deleterious effects of oxygen limitation in vital organs. This enables the fetus to survive asphyxia intact unless the insult is profound or prolonged. The most common asphyxial stresses imposed on the fetus during labor are insufficiency of uterine blood flow, or insufficiency of umbilical blood flow, and occasionally decrease in uterine arterial oxygenation.

The wording Operative Delivery or Operational Delivery means caesarean section (CS) and Instrumental delivery.

The wording Instrumental delivery means forceps delivery and Vacuum extraction.

The wording Operative Delivery due to Fetal Distress (ODFD) means caesarean section (CS) and/or instrumental delivery such as forceps delivery and/or vacuum extraction, which is performed on the term pregnant subject for delivering the baby in cases where there are signs of the fetus not being well (i.e. fetal distress).

The wording partus means culmination of a woman's pregnancy period with delivery of a baby.

The wording uncomplicated delivery (uncomplicated partus) means that a woman can manage to deliver a baby without the need for intervention such as caesarian section, or the need to use instrumental delivery.

Response group I means subjects in the clinical study PPL17 as herein disclosed, who enter into spontaneous onset of labor after having been treated with from 1-7 doses of tafoxiparin.

Response group II means subjects in the clinical study PPL17 as herein disclosed, who are given 4-7 doses of tafoxiparin without entering into spontaneous onset of labor, but which subjects achieves a ripe cervix (defined as a Bishop Score≥6). A subject in response group II may be induced into labor according to normal Standard of Care such as amniotomy and oxytocin treatment, but not prior to 4 treatment doses of tafoxiparin has been given.

Response group III means subjects in the clinical study PPL17 as herein disclosed, who have been treated with 7 doses of tafoxiparin without entering into spontaneous onset of labor, and which subjects have an unripe cervix. A subject in response group III shall be treated with a cervical balloon catheter which shall remain in the cervix until it is expelled, or up to a maximum of 24 hours. If the cervix is still unripe after 24 hours of balloon catheter treatment, the subject is treated with oral PGE-1 according to clinical routines. When the cervix is ripe (Bishop Score ≥6), the patient should be induced into labor with amniotomy and oxytocin. If the subject does not enter into labor after PGE-1 and oxytocin treatment, the subject shall be managed at the discretion of the treating physician.

Response group IV means subjects in the clinical study PPL17 as herein disclosed, which subjects require induction into labor prior to having been treated with 7 doses of tafoxiparin, due to medical reasons.

The wording NICU as used in the clinical study PPL17 as herein disclosed, means neonatal intensive care unit.

Throughout the patent specification and claims, the wording subject, patient and woman may be used interchangeably, and means a term pregnant women as defined herein.

The singular forms "a", "an" and "the" may also be referred to in pluralis.

The wording IUGR means Intrauterine growth restriction, and is a term used when the baby in the womb (a fetus) does not grow as expected and is not as big as would be expected for the stage of the mother's pregnancy (i.e. an unborn baby's gestational age). The reason for IUGR may be insufficient nutrition, blood flow and oxygen to the fetus of the placenta.

The wording CTG recording means cardiotocography, and is in obstetrics a technical method for recording (-graphy) the fetal heartbeat using ultrasound (cardio-) and the uterine contractions (-toco-) during pregnancy. The machine which is used to perform the monitoring is called a cardiotocograph, commonly known as a fetal monitor.

Tocolytics are anti-contraction medications or labor suppressant medications used to suppress premature labor. Commonly used tocolytic medications include $\delta_2$ agonists, calcium channel blockers, NSAIDs, and magnesium sulfate. These can assist in delaying preterm delivery by suppressing uterine muscle contractions and their use is intended to reduce fetal morbidity and mortality associated with preterm birth.

Apgar score is a scoring system which is commonly used by an obstetrician to assess the oxygen level of a new-born baby and the risk of asphyxia. The assessment comprises 5 parameters which may each give 0 to 2 points (i.e. a maximum of 10 points at each time point for Apgar assessment). The assessment is usually performed at 1, 5 and 10 minutes after delivery on all neonates, and thereafter every 5 minutes in case of continued neonatal surveillance.

Pharmaceutical Formulations and Administration Routes

Tafoxiparin as used in accordance with the invention, may be administered as a pharmaceutical composition suitable for systemic administration. Examples of systemic administration include parenteral administration, such as by subcutaneous administration, intravenous injection or intramuscular administration.

Tafoxiparin as used in accordance with the invention, may also be administered by local administration. Examples of local administration that may be useful in administering the tafoxiparin in accordance with the invention include oral administration, vaginal administration or rectal administration.

For parenteral administration, tafoxiparin may be incorporated into a solution or suspension, which may also contain one or more adjuvants such as sterile diluents such as water for injection, saline, fixed oils, polyethylene glycol, glycerol, propylene glycol or other synthetic solvents, antibacterial agents, antioxidants, chelating agents, buffers and agents for adjusting the osmolality. The parenteral pharmaceutical formulation may be filled into ampoules, vials, disposable syringes or as infusion arrangements, such as for self-administration.

In one aspect of the invention, tafoxiparin as described in accordance with the invention, is for use by self-administration by the pregnant woman in an out-patient setting.

EXAMPLES

Manufacture of Tafoxiparin

Tafoxiparin, as described and used in accordance with the invention, may be prepared by following the synthetic procedure as described in Examples 1 to 9 of the published patent application WO 2013/095279 or Examples 1 to 3 of WO 2014/202982.

In the myograph experiments performed below, tafoxiparin was provided by Dilafor AB, Sweden, as a 150 mg/mL solution:

| Ingredient | Concentration | Function |
|---|---|---|
| Tafoxiparin (DF01) | 150 mg/mL | API |
| Sodium phosphate | 15 mM | pH buffer |
| Hydrochloric acid | As required | pH adjuster |
| Sodium hydroxide | As required | pH adjuster |
| Water for injection | Ad 1 ml | Solvent/Diluent |

Clinical Phase II Trial

A clinical phase II trial is performed as a randomized, double-blind, placebo-controlled, parallel-group proof of concept study (Part A) with a conditional dose finding follow up study (Part B) to evaluate the efficacy, safety, tolerability and dose response of subcutaneously administered tafoxiparin as a supplement to induction therapy in term pregnant, nulliparous women with an unripe cervix. The study is performed in Sweden and Finland (PPL17), and an EMA (European Medicines Agency) description of the study can be found on the EU Clinical Trials Register web (www.clinicaltrialsregister.eu/ctr-search/search?query=PPL17).

A total of 170 term pregnant women are randomized to receive either 300 mg of tafoxiparin, or corresponding placebo (vehicle), administered subcutaneously every 24±3 hours and up to a total of 7 doses, or until partus (Part A).

In the dose finding follow up study (Part B), a total of 164 term pregnant women are randomized to receive either 75 or 150 mg of tafoxiparin administered subcutaneously every 24±3 hours from start of labor induction and up to a total of 7 doses, or until partus.

Subjects who enter into 37 weeks of gestation may be subject to the informed consent procedure.

Primary Objectives

To assess the efficacy of tafoxiparin on cervical ripening/cervical ripening rate, during and up to the first seven days of treatment, measured by Bishop score. All women must be examined to check the cervical state before enrollment.

Secondary Objectives

To assess the maternal and neonatal safety, tolerability and dose response of tafoxiparin as a supplement therapy in term pregnant, nulliparous women with an unripe cervix undergoing labor induction.

The Following Endpoints Will be Monitored:

Time from start of treatment to increase in Bishop score of ≥2 points or spontaneous onset of labor, whichever comes first. Time from start of treatment to increase in Bishop score of ≥3 points or spontaneous onset of labor, whichever comes first. Time from start of treatment to increase in Bishop score of ≥4 points or spontaneous onset of labor, whichever comes first.

Cervical ripening as measured by change from baseline to end of treatment in Bishop Score.

Time from onset of labor to partus, where onset of labor is defined as last record of 4 cm cervical dilatation visualized in the partogram and progress of labor, or last record of 4 cm of cervical dilatation in combination with amniotomy and intravenous administration oxytocin.

Proportion of women with labor time ≤8 hours.

Proportion of women with established labor ≥12 hours.

Total dosages of study drug (IMP).

Proportion of women with spontaneous onset of labor (Response group I).

Proportion of women with a ripe cervix (Response group I+II+μI).

Proportion of women who must be induced into labor for medical reasons according to clinical practice (Response group IV).

Study Drug (Investigational Medical Product, IMP)

Part a of the Study:

Tafoxiparin/Placebo is supplied by Dilafor AB to the site as kits designed to constitute 300 mg of tafoxiparin or placebo for daily administration. Apart from the active substance, each ml of study drug will constitute 0.015 M phosphate buffer. The study medication kit for each patient will contain 8 doses consisting of 2 vials containing a minimum extractable volume of 1.6 ml of 150 mg/ml of tafoxiparin or placebo. One dose is a reserve dose in case a dose is rendered unusable. The investigational product should be administered subcutaneously every 24±3 hours by the site staff for up to 7 doses, or until partus. At each dosing time 1.0 ml of the drug will be extracted from each of the 2 vials and injected as separate s.c. injections in the abdominal or hip region.

Part B of the Study:

Tafoxiparin/Placebo is supplied by Dilafor AB to the site as kits designed to constitute 75 or 150 mg of tafoxiparin for daily administration. Apart from the active substance, each ml of study drug will constitute 0.015 M phosphate buffer. The study medication kit for each patient will contain 8 doses consisting of 2 vials for each injection occasion containing a minimum extractable volume of 1.6 ml of 150 mg/ml of tafoxiparin or placebo. For subjects receiving 75 mg of tafoxiparin, one vial will contain active substance and one containing placebo. For subjects receiving 150 mg of tafoxiparin, both vials will contain active substance. One dose is a reserve dose in case a dose is rendered unusable. The investigational product should be administered subcutaneously every 24±3 hours by the site staff for up to 7 doses, or until partus. At each dosing time, 0.5 ml of the drug will be extracted from each of the 2 vials and injected as separate s.c. injections in the abdominal or hip region.

Investigational Product (Placebo):

Matching placebo saline solution will be supplied to the site containing 9 mg/ml of sodium chloride (NaCl) solution. The placebo saline solution will be indistinguishable from the active solutions in appearance, smell and packaging.

Non-Investigational Product:

The cervical state will be checked and in women with a Bishop score below 6 after 7 days, a balloon catheter is inserted, the balloon catheter is expelled or retracted after maximum 24 hours. If balloon catheter treatment is unsuccessful, treatment with oral PGE-1 may be administered according to clinical practice. The cervical balloon catheters and the PGE-1 will be supplied by the hospital. In case of a ripe cervix (usually at a Bishop score ≥6 as scored by the responsible physician) after 4-7 injections, amniotomy and oxytocin may be used in order to induce labor.

Study Treatment and Induction of Labor

If the subject is found to be eligible for the study, she will be randomized to study treatment, i.e. 300 mg of tafoxiparin or corresponding placebo daily (Part A), or 75 or 150 mg daily (Part B).

If Baseline occurs 24 hours after Screening, Inclusion/Exclusion Criteria, Vital Signs, Cervical Palpation and Concomitant Medication (Mother) will not be repeated prior to treatment with IMP.

The subject is included in the study when study treatment is initiated by the first injection of the IMP.

In Part A of the study, the daily dose of tafoxiparin will be 300 mg administered once daily.

In Part B of the study, the daily dose of tafoxiparin will be 150 mg or 75 mg, administered once daily.

At every daily dosing instance, the subject will receive SC injections.

The study medication will be administered subcutaneously in the abdominal or hip region for up to a total of 7 doses or until labor induction or spontaneous onset of labor. If the cervix is still unripe after 7 doses of IMP, the patient is given cervical balloon catheter as a mean of labor induction.

Cervical palpation should be performed daily. Membrane sweeping to initiate labor should not be performed during the treatment of IMP and before a ripe cervix.

Response Group I

Subjects who enter into spontaneous onset of labor after 1-7 doses of IMP should be managed according to clinical routines.

Response Group II

Subjects who are given 4-7 doses without entering into spontaneous onset of labor, but with a ripe cervix (Bishop Score ≥6), should be induced into labor by amniotomy and oxytocin treatment, but not before 4 treatment doses have been given.

Response Group III

Subjects who are given 7 doses of IMP without entering into spontaneous onset of labor and with an unripe cervix, shall be treated with a cervical balloon catheter provided by the hospital according to instructions provided by the sponsor. The balloon catheter should stay in the cervix until it is expelled or up to 24 hours. If the cervix is still unripe after 24 hours of balloon catheter treatment, the subject should be given PGE-1 treatment orally according to clinical routine. When the cervix is ripe (Bishop Score ≥6), the patient should be induced into labor with amniotomy and oxytocin. If they do not enter into labor after PGE-1 and oxytocin treatment, they should be managed at the discretion of the treating physician.

A CTG recording should be performed in relation to PGE-1 treatment according to clinical practice. Abnormal CTG with signs of hypercontractility will be treated according to clinical routines and with tocolytics if needed.

Response Group IV

The subject must be induced into labor before 7 doses of IMP have been given due to medical reasons or subjects demand. They should be managed according to clinical practice.

Conduct of the Trial

The following procedures are repeated every 24 hour or until a ripe cervix (Bishop Score 6) has been registered:

Cervical palpation and Bishop score
Vital signs (Blood pressure (maternal), heart rate (maternal)
Cardiotocography (Fetal surveillance)
Study drug administration
Injection site reactions
Concomitant medication (maternal)
Adverse events (maternal/fetal)

If balloon catheter treatment is instituted after 7 days of IMP treatment the following procedures are conducted when the balloon catheter is expelled or after 24 hours.

Vital signs (Blood pressure, heart rate)
Cervical palpation after 24 hours or when the balloon catheter is expelled
Injection site reactions
Concomitant medication (maternal)
Adverse events (maternal/fetal)

If the cervix still is unripe after 24 hours of balloon catheter treatment, oral PGE-1 treatment may be given according to clinical practice. A CTG recording during 20-30 minutes before and 1 hour after every dose of PGE-1 should be performed. Adverse events (maternal/fetal) should be recorded.

Secondary Safety and Tolerability Endpoints Include:

1. Proportion of patients undergoing caesarean sections (CS).
2. Proportion of patients undergoing instrumental deliveries (vacuum extraction (VE)/forceps delivery).
3. Fetal outcome measured as Birth weight, Apgar score, Acidosis (pH<7.10) and/or Base Excess <−12 mmol/L arterial or venous in umbilical cord blood.
4. Indications for Operational delivery.
5. Proportion of Fetal Distress.
6. Indication for referral to neonatal intensive care unit (NICU).
7. Proportion of infants staying in the NICU for >48 hours.
8. Uterine hyper stimulation in demand of tocolytic treatment.
9. Proportion of patients with Postpartum Hemorrhage (PPH) >2000 ml.

Selection Criteria

Inclusion

In order to participate in this study, the subjects must meet all of the following inclusion criteria: Pregnant women of ≥18 and ≤64 years of age who are nulliparous, have an unripe cervix with ≤4 points according to Bishop score (0-10 points scale), and who are planned for labor induction after 4-7 days of IMP treatment.

Gestational age ≥37 weeks confirmed by ultrasound before 21 weeks of gestation. Singleton pregnancy. Subject is, as per the discretion of the Investigator, able to comply with the requirements of the protocol including an ability to be present at all required controls The Investigator is responsible for obtaining signed informed consent from all subjects before including the subject in any study related procedures.

Examples of diagnosis as a basis for induction are post term pregnancy (40-41 weeks of gestation), gestational diabetes, diabetes type 1 (well controlled), pre-eclampsia (BP diastolic <100, systolic <140), hypertension (well controlled), hepatosis (without clinically significantly elevated serum bile acids), maternal age >40 years, humanitarian-psycho social reasons, and/or oligohydramnios.

Exclusion

In order to participate in the study subjects must not meet any of the following exclusion criteria: Subjects who are unable to understand the written and verbal instructions in local language; breech presentation and other abnormal fetal presentations; previous uterine scar; spontaneous rupture of membranes at inclusion; pathologic CTG at inclusion; fetal estimated weight >2SD of normal fetal estimated weight earlier diagnosed by ultrasound and documented in patient record; mother's BMI >35 at early pregnancy; known IUGR defined as ≤2SD of normal; presence of eclampsia; severe pre-eclampsia; HELLP syndrome (hemolysis, elevated liver enzymes, and low platelets); clinically significant vaginal bleeding in need of hospitalization in the third trimester; placenta previa; previously known coagulation disorders (Leiden, heterozygote—OK); treatment with a heparin/LMWH product during the previous six months; current use of any drugs that interfere with hemostasis such as oral anti-coagulant medication, non-steroidal anti-inflammatory drugs (NSAID) compounds and vitamin K antagonists; current use of acetylsalicylic acid (ASA) compounds or use within the week preceding inclusion; diagnosed with HIV or Acute hepatitis; known history of allergy to standard heparin and/or LMWH heparin; history of heparin-induced thrombocytopenia; current drug or alcohol abuse which in the opinion of the Investigator should preclude participation in the study; current participation in other interventional medicinal treatment studies; subject has a fear of needles which is believed by the Investigator to affect study medication compliance; any relevant condition, laboratory value or concomitant medication which, in the opinion of the investigator, makes the subject unsuitable for entry into the study.

Labor

The onset of labor is defined as last record of 4 cm cervical dilatation visualized in the partogram and progress of labor, or last record of 4 cm of cervical dilatation in combination with amniotomy and intravenous administration oxytocin.

CTG registration will be performed continuously during established labor.

If slow progress of labor (cervical dilation <1 cm per/hour during 3 hours) or labor arrest (no progress during 3 hours) occur in patients who are not yet on oxytocin treatment, they should be given oxytocin treatment according to clinical practice.

The characteristics of the new-born baby will be evaluated and recorded.

Arterial or venous umbilical cord blood will be collected for analyses of Acidosis (pH<7.10) and/or Base Excess <−12 mmol/L After labor, the subject will remain at the clinic as per clinical practice until the Discharge.

The primary efficacy endpoint is "Cervical ripening rate during up to the first seven days of treatment, measured by Bishop Score".

65% of the women who entered into part in Part A of this clinical study, had a Bishop score of 0-2, and 35% of the women who entered into Part A of the study had a Bishop score of 3-4.

Results

As shown in FIG. 1, 41.1% of women treated with 300 mg tafoxiparin (37 women of 90) achieved spontaneous onset of labor (p-value=0.089; the p-value for part A of the study was 0.080). 42.4% of women treated with 150 mg tafoxiparin (36 women of 85) achieved spontaneous onset of labor (p-value 0.039). 40.2% of women treated with 75 mg tafoxiparin (33 women of 82) achieved spontaneous onset of labor (p-value 0.102). Only 28.7% of women treated with placebo (25 women of 87) achieved spontaneous onset of labor.

Hence, tafoxiparin in all three doses 300 mg, 150 mg and 75 mg respectively, was effective for achieving spontaneous onset of labor.

Figure 2:
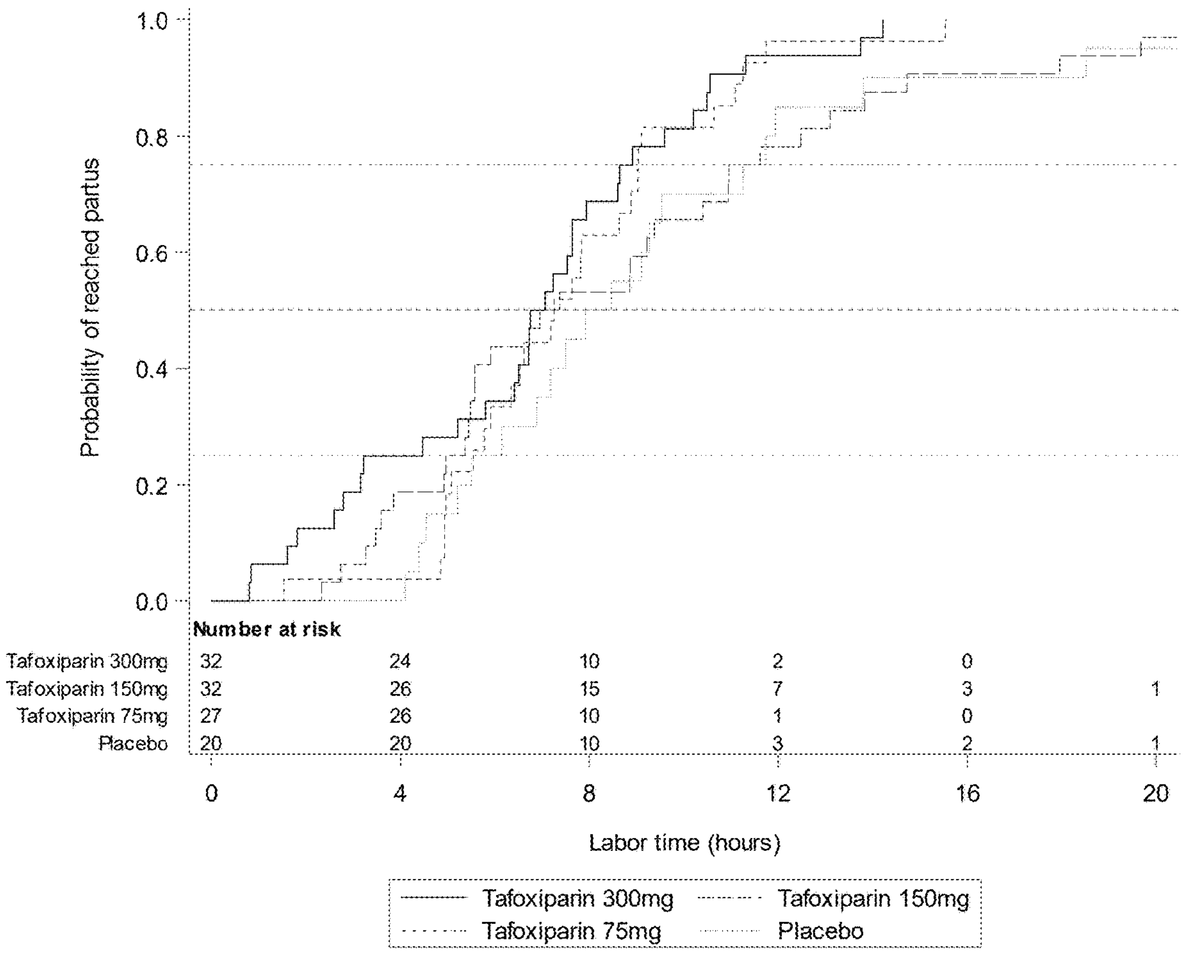
FIG. 2 is a statistical analysis of labor time for women in response group I (Kaplan-Meier plot, Vaginal delivery population). The figure shows labor time up to the time for vaginal delivery (partus) for women with spontaneous onset of labor and which women have been treated with 300 mg tafoxiparin, 150 mg tafoxiparin, 75 mg tafoxiparin, and placebo, respectively.

FIG. 2 shows labor time up to the time for vaginal delivery (partus) for women with spontaneous onset of labor and which had been treated with 300 mg tafoxiparin (p-value=0.070), 150 mg tafoxiparin (p-value 0.654) and 75 mg tafoxiparin (p-value 0.114), respectively, compared to women who had been treated with placebo. The data shows that women that had been treated with tafoxiparin did not only have a spontaneous onset of labor, but they also had a shorter labor time up to vaginal delivery (partus) compared to placebo.

Figure 3:
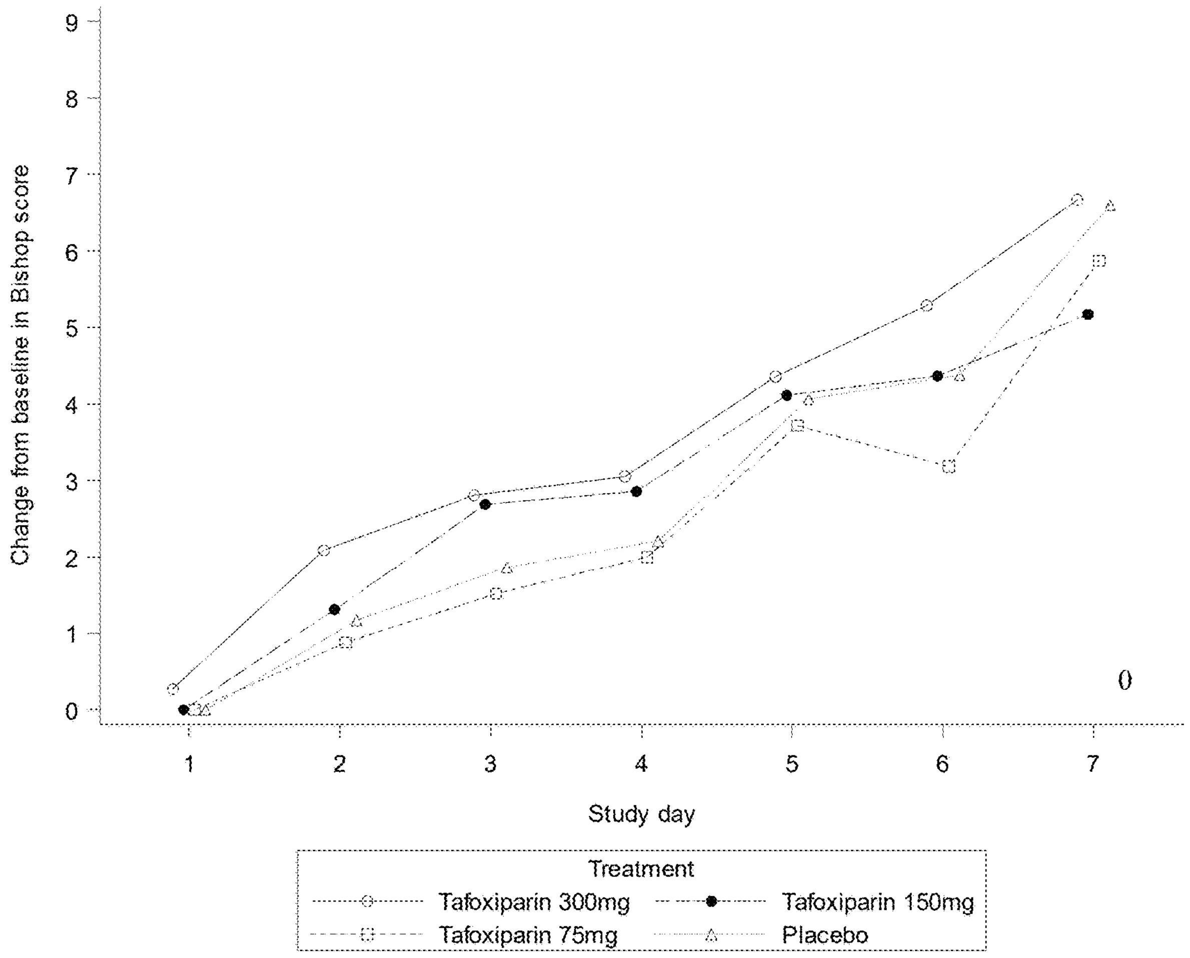
FIG. 3 shows change of Bishop score (ripeness of cervix) in women treated with 300 mg tafoxiparin, 150 mg tafoxiparin, 75 mg tafoxiparin, and placebo respectively, and having a spontaneous onset of labor.

FIG. 3 shows change of Bishop score (ripeness of cervix) in women treated with 300 mg tafoxiparin, 150 mg tafoxiparin and 75 mg tafoxiparin, and placebo, respectively, and with spontaneous onset of labor. As shown in this figure, the data clearly indicate that women treated with 300 mg tafoxiparin and 150 mg tafoxiparin respectively, achieved spontaneous onset of labor at an earlier time point than women treated with 75 mg tafoxiparin and placebo, respectively. This data also supports that tafoxiparin in the doses 300 mg and 150 mg, both have a beneficial effect on cervical ripening.

Figure 4:
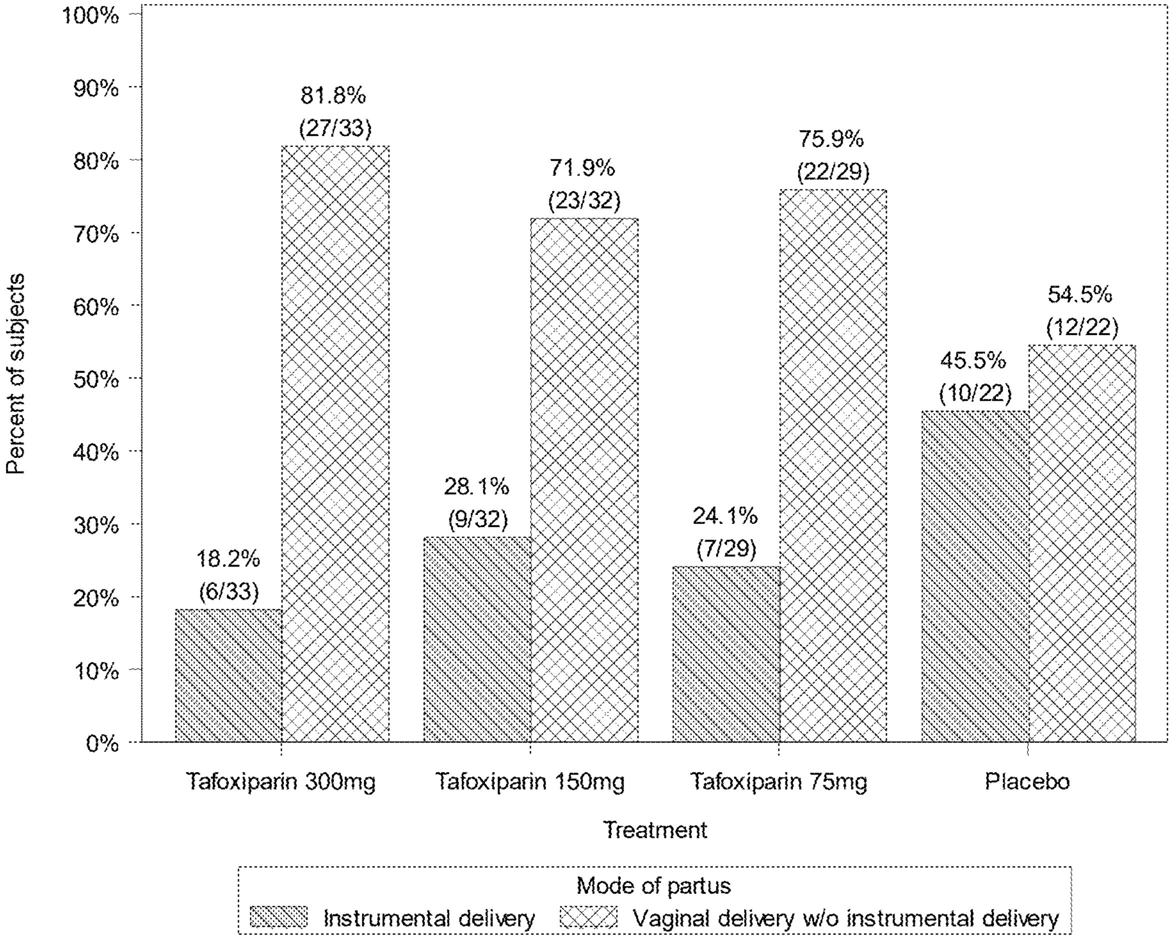
FIG. 4 shows the vaginal mode of partus for women treated with 300 mg tafoxiparin, 150 mg tafoxiparin, 75 mg tafoxiparin, and placebo respectively, and with a spontaneous onset of labor.

FIG. 4 shows the vaginal mode of partus for women treated with 300 mg tafoxiparin, 150 mg tafoxiparin and 75 mg tafoxiparin, and placebo, respectively, and with a spontaneous onset of labor. As seen in the graph, of the women who reached spontaneous onset of labor, only 18.2% of women (6 of the 33 women) treated with 300 mg tafoxiparin needed instrumental delivery (p-value=0.048) (the p-value for part A of the study was 0.053). Of the women who had been treated with 150 mg tafoxiparin and with a spontaneous onset of labor, only 28.1% (9 of the 32 women) needed instrumental delivery (p-value 0.422). Of the women who had been treated with 75 mg tafoxiparin and with a spontaneous onset of labor, only 24.1% (7 of the 29 women) needed instrumental delivery (p-value=0.181). For women treated with placebo and with a spontaneous onset of labor, 45.5% (10 of the 22 women) needed instrumental delivery.

This means that for the women treated with 300 mg tafoxiparin, 81.8% (27 of the 33 women) reached spontaneous onset of labor with uncomplicated delivery. For the women treated with 150 mg tafoxiparin, 71.9% (23 of the 32 women) reached spontaneous onset of labor with uncomplicated delivery, and the women treated with 75 mg tafoxiparin, 75.9% (22 of the 29 women) reached spontaneous onset of labor with uncomplicated delivery. In the placebo group, only 54.5% (12 of the 22 women) reached spontaneous onset of labor and uncomplicated vaginal delivery.

In conclusion, all three doses of tafoxiparin (300 mg, 150 mg and 75 mg) were effective in reducing the need for instrumental delivery in women with a spontaneous onset of labor, compared to placebo.

Figure 5:
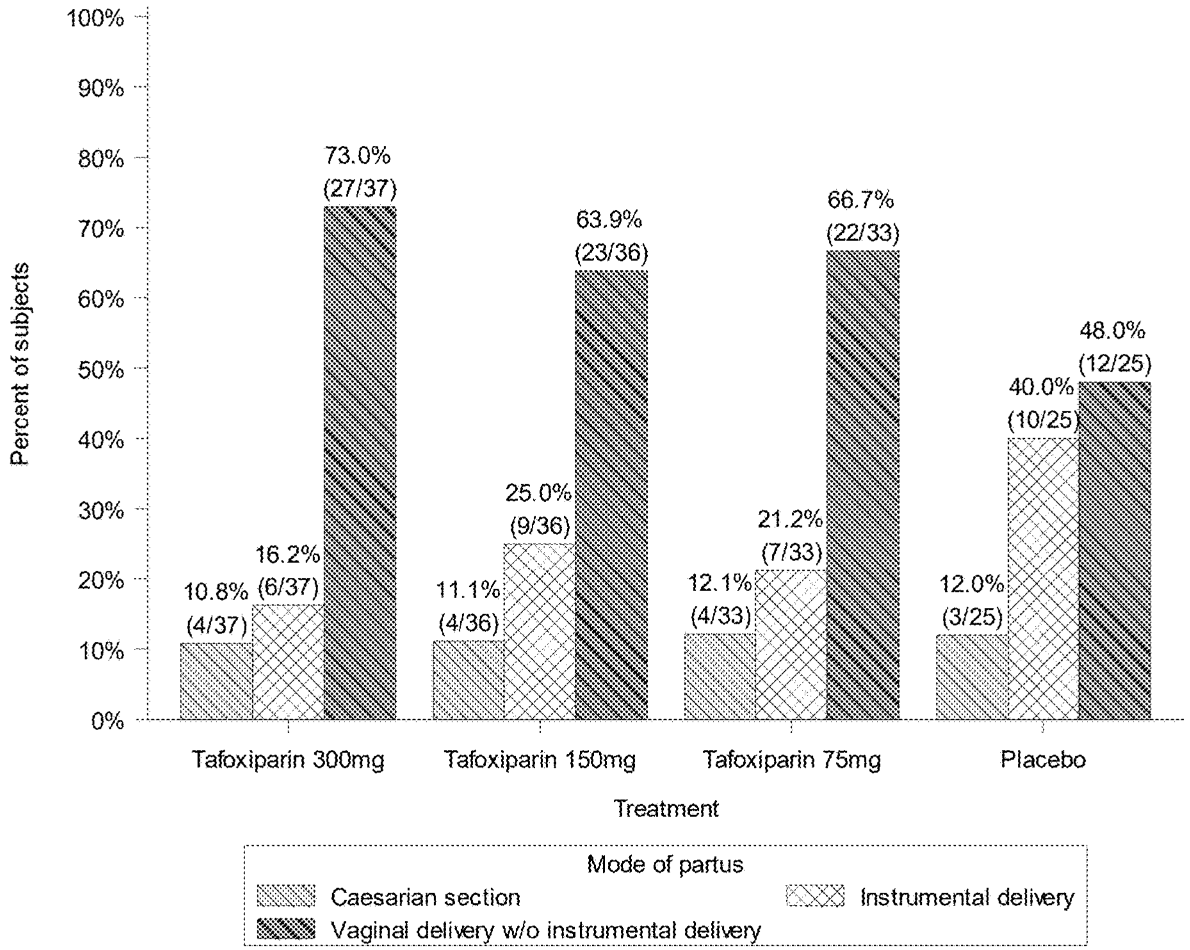
FIG. 5 shows the mode of partus for women treated with 300 mg tafoxiparin, 150 mg tafoxiparin, 75 mg tafoxiparin, and placebo respectively, and with a spontaneous onset of labor.

FIG. 5 shows the mode of partus for women with a spontaneous onset of labor and treated with 300 mg tafoxiparin, 150 mg tafoxiparin, 75 mg tafoxiparin and placebo, respectively. As seen in the graph, the following results were obtained for the women with spontaneous onset of labor: 73% (i.e. 27 of the 37 women) treated with 300 mg tafoxiparin reached partus by vaginal delivery and with no need for instrumental delivery, nor caesarian section. 63.9% (23 of 36 women) treated with 150 mg tafoxiparin reached partus by vaginal delivery and with no need for instrumental delivery nor caesarian section. 66.7% (22 of 33 women) treated with 75 mg tafoxiparin reached partus by vaginal delivery and with no need for instrumental delivery nor caesarian section. For the group of women treated with placebo, only 48% (i.e. 12 of the 25 women) reached partus by vaginal delivery and with no need for instrumental delivery nor caesarian section.

This graph also shows that of the women with spontaneous onset of labor and treated with 300 mg tafoxiparin, only 27% of women (i.e. 10 of the 37 women) needed instrumental delivery or caesarian section to reach partus. In the women with spontaneous onset of labor and treated with 150 mg tafoxiparin, only 36.1% of women (13 of 36 women) needed instrumental delivery or caesarian section to reach partus. In the women with spontaneous onset of labor and treated with 75 mg tafoxiparin, only 33.3% of women (11 of 33 women) needed instrumental delivery or caesarian section to reach partus. This should be compared with the placebo group, where 52% of women (i.e. 13 of the 25 women) treated with placebo needed instrumental delivery or caesarian section.

From this data, it can be concluded that tafoxiparin in all three doses 300 mg, 150 mg and 75 mg, was effective for a woman to reach partus by vaginal delivery and with less need for instrumental delivery or caesarian section, compared to placebo.

Effect of Tafoxiparin for the Onset of Labor with Intervention

The effect of 300 mg, 150 mg and 75 mg tafoxiparin for the onset of labor with intervention, was compared with placebo.

The results are shown in Table 1 below.

TABLE 1

Onset of labor with intervention

| Parameter | Tafoxiparin 300 mg [n = 91] | Tafoxiparin 150 mg [n = 85] | Tafoxiparin 75 mg [n = 83] | Placebo [n = 88] | Total no. of subjects in Parts A and B [n = 347] |
|---|---|---|---|---|---|
| Labor induced | 53 (58.2%) | 48 (56.5%) | 48 (57.8%) | 62 (70.5%) | 211 (60.8%) |
| Labor induction with Balloon catheter | 42 (46.2%) | 37 (43.5%) | 35 (42.2%) | 51 (58.0%) | 165 (47.6%) |
| Labor induced with oxytocin | 45 (49.5%) | 38 (44.7%) | 34 (41.0%) | 48 (54.5%) | 165 (47.6%) |
| Labor induced with amniotomy | 50 (54.9%) | 39 (45.9%) | 46 (55.4%) | 50 (56.8%) | 185 (53.3%) |
| Labor induced with PGE-1 | 5 (5.5%) | 7 (8.2%) | 7 (8.4%) | 9 (10.2%) | 28 (8.1%) |

As shown in Table 1, the following surprising results were achieved:

a. 70.5% of the women treated with placebo needed some type of intervention for labor induction, compared to only 58.2% for women having been treated with 300 mg tafoxiparin, 56.5% for women having been treated with 150 mg tafoxiparin, and 57.8% for women having been treated with 75 mg tafoxiparin.
b. 58.0% of the women in the placebo group were subjected to the use of a balloon catheter to induce the woman into labor, compared to only 46.2% in the group having been treated with 300 mg tafoxiparin, 43.5% for women having been treated with 150 mg tafoxiparin, and 42.2% for women having been treated with 75 mg tafoxiparin.
c. 54.5% of the women in the placebo group were subjected to oxytocin treatment to induce the woman into labor, compared to only 49.5% in the group having been treated with 300 mg tafoxiparin, 44.7% for women having been treated with 150 mg tafoxiparin, and 41.0% for women having been treated with 75 mg tafoxiparin.
d. 56.8% of the women in the placebo group were subjected to amniotomy to induce the woman into labor, compared to only 54.9% in the group having been treated with 300 mg tafoxiparin, 45.9% for women having been treated with 150 mg tafoxiparin, and 55.4% for women having been treated with 75 mg tafoxiparin.
e. 10.2% of the women in the placebo group were subjected to PGE-1 treatment to induce the woman into labor, compared to only 5.5% in the group having been treated with 300 mg tafoxiparin, 8.2% for women having been treated with 150 mg tafoxiparin, and 8.4% for women having been treated with 75 mg tafoxiparin.

In conclusion, tafoxiparin in all three doses reduced the need for intervention in order to achieve onset of labor, compared to placebo.

Fetal Distress

Fetal distress was evaluated in women that had undergone Operative Delivery (i.e. caesarean section or instrumental delivery) and having been treated with 300 mg tafoxiparin, 150 mg tafoxiparin, 75 mg tafoxiparin and placebo, respectively.

The results are shown in Table 2 below.

TABLE 2

Effect of tafoxiparin on Operative delivery for fetal distress (ODFD).

| | Tafoxiparin 300 mg [n = 91] | Tafoxiparin 150 mg [n = 85] | Tafoxiparin 75 mg [n = 83] | Placebo [n = 88] | Total [n = 347] |
|---|---|---|---|---|---|
| Number of patients with operative delivery | 32 (35.2%) | 41 (48.2%) | 32 (38.6%) | 40 (45.5%) | 145 (41.8%) |
| Fetal distress as indication for operative delivery | 11 (12.1%) | 20 (23.5%) | 16 (19.3%) | 20 (22.7%) | 67 (19.3%) |

As seen in Table 2, of the 91 women having been treated with 300 mg tafoxiparin, 11 women (12.1%) required operative delivery due to fetal distress (ODFD). Of the 85 women that had been treated with 150 mg tafoxiparin, 20 women (23.5%) required operative delivery due to fetal distress (ODFD). Of the 83 women that had been treated with 75 mg tafoxiparin, 16 women (19.3%) required operative delivery due to fetal distress (ODFD).

In comparison, 20 women out of 88 women who had received placebo, required operative delivery (22.7%) due to fetal distress.

Spontaneous Onset of Labor

During this clinical study, a day-by-day monitoring was also performed during the first seven days of treatment with 300 mg tafoxiparin, 150 mg tafoxiparin and 75 mg tafoxiparin, and placebo, to monitor the number of subjects (women) who had achieved a spontaneous onset of labor. The results are shown in Table 3 below:

TABLE 3

Summary of number of subjects (women) that reach spontaneous onset of labor.

| Treatment | n | Study day 1 | Study day 2 | Study day 3 | Study day 4 | Study day 5 | Study day 6 | Study day 7 | Study day 8 | Study day 9 |
|---|---|---|---|---|---|---|---|---|---|---|
| Tafoxiparin 300 mg | 37 | 2 (5%) | 11 (30%) | 18 (49%) | 23 (62%) | 30 (81%) | 34 (92%) | 37 (100%) | N/A | N/A |
| Tafoxiparin 150 mg | 36 | 0 (0%) | 4 (11%) | 15 (42%) | 19 (53%) | 26 (72%) | 30 (83%) | 34 (94%) | 35 (97%) | 36 (100%) |
| Tafoxiparin 75 mg | 33 | 0 (0%) | 3 (9%) | 6 (18%) | 11 (33%) | 22 (67%) | 25 (76%) | 32 (97%) | 33 (100%) | N/A |
| Placebo | 25 | 0 (0%) | 2 (8%) | 5 (20%) | 7 (28%) | 16 (64%) | 20 (80%) | 25 (100%) | N/A | N/A |

n = number of subjects (women)

As seen in Table 3, the development day-by-day towards a spontaneous onset of labor, shows a dose-response relationship (i.e. the response in efficacy as a function of exposure to the drug tafoxiparin). The wording "N/A" in the Table 3, means that at the particular study day, there were no remaining subjects (women) that had not reached spontaneous onset of labor.

Cervical Ripening Rate During the First Seven Days of Treatment

The estimated cervical ripening rate was measured by Bishop score during the first 7 days of treatment with all three doses of tafoxiparin (300 mg, 150 mg and 75 mg), as well as treatment with placebo. The wording "estimated cervical ripening rate" means an estimate of the magnitude of cervical ripening rate, based on observed values for the Bishop score.

Figure 6:
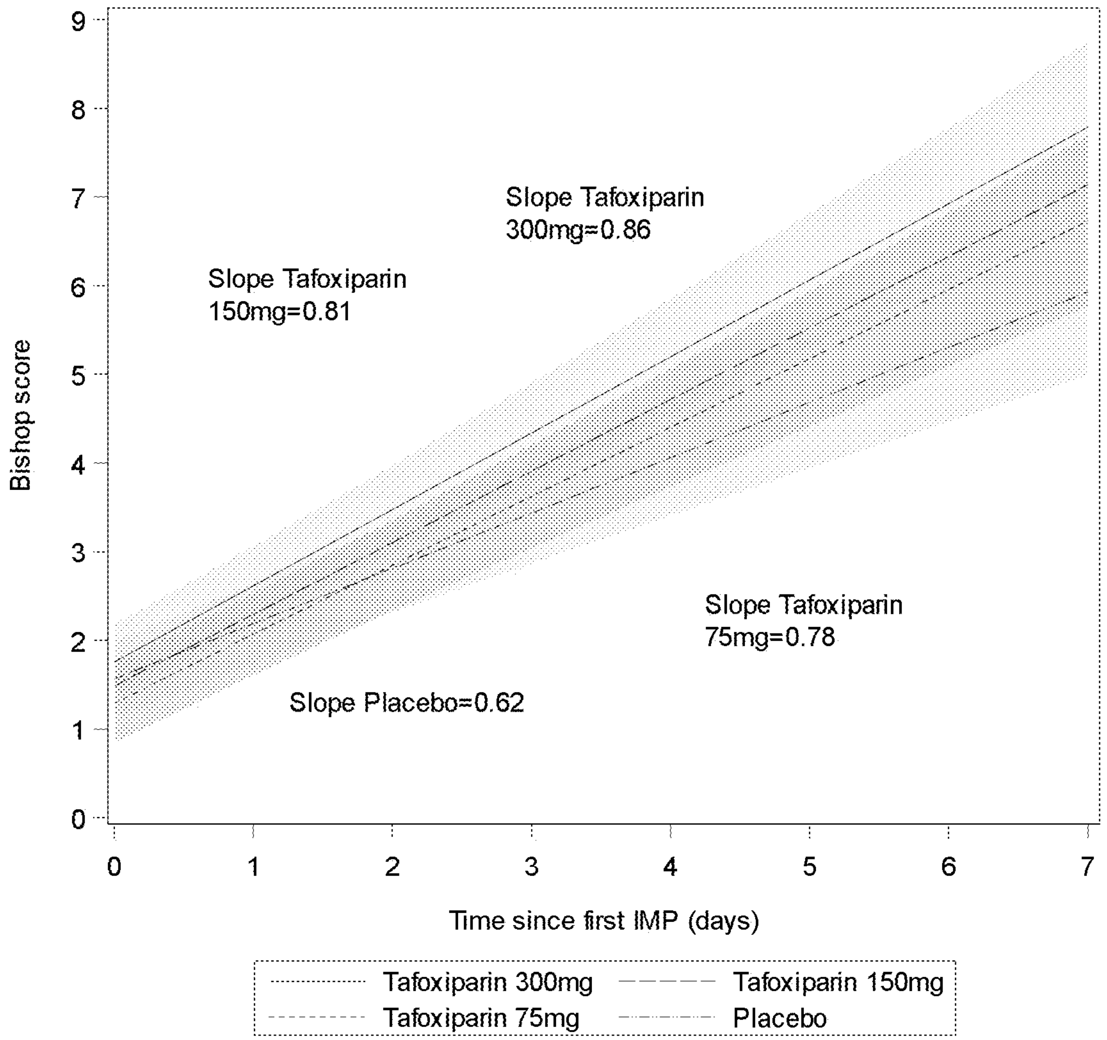
FIG. 6 shows the cervical ripening rate measured by Bishop score, during the first seven days of treatment with 300 mg tafoxiparin, 150 rng tafoxiparin, 75 mg tafoxiparin, and placebo respectively.

As shown in FIG. 6, the cervical ripening rate was higher in women having been treated with all three doses of tafoxiparin (300 mg, 150 mg and 75 mg) compared to women having been treated with placebo. These results also support a dose-response relationship (i.e. the response in efficacy as a function of exposure of the drug tafoxiparin).

CONCLUSIONS

The results of this clinical study show that tafoxiparin in a daily dose of 75 mg, 150 mg and 300 mg, is effective in spontaneous onset of labor, and either puts the woman in a ready stage of labor and partus when used as monotherapy, or reduces the need to use standard of care therapy in women that have been treated with any one of the three doses 75 mg, 150 mg and 300 mg of tafoxiparin. Moreover, the results show a reduction of the need for operative delivery (i.e. caesarean section and instrumental delivery) due to fetal distress. The results also show that women who have been treated with tafoxiparin in any one of the three doses 75 mg, 150 mg and 300 mg of tafoxiparin achieve a ripe cervix at an earlier time point than women that have been treated with placebo, which in turns provides an earlier onset of labor and an uncomplicated partus.

What is claimed is:

1. A method for the spontaneous onset of labor in a term pregnant woman in need thereof, the method comprising administering a therapeutically effective amount of tafoxiparin in a daily dose of 75 to 320 mg per day, as a monotherapy, to said term pregnant woman.

2. The method according to claim 1, wherein the term pregnant woman is in gestation week 36-42.

3. The method according to claim 1, wherein the woman has an unripe cervix.

4. The method according to claim 1, wherein the woman has a Bishop score of 6 or less.

5. The method according to claim 1, the method comprising administering tafoxiparin once daily.

6. The method according to claim 1, the method comprising administering tafoxiparin to the term pregnant woman for up to 14 days.

7. The method according to claim 1, wherein said term pregnant woman is a nulliparous woman.

8. The method according to claim 1, wherein said method is for labor priming.

9. The method according to claim 1, wherein said method comprises cervical ripening.

10. The method according to claim 1, the method comprising administering tafoxiparin by parenteral administration.

11. The method according to claim 1, the method comprising administering tafoxiparin by local administration.

12. The method according to claim 10, wherein the parenteral administration is intravenous administration, intramuscular administration or subcutaneous administration.

13. The method according to claim 11, wherein the local administration is oral administration, vaginal administration or rectal administration.

14. The method according to claim 1, wherein said method is for self-administration by the pregnant woman in an out-patient setting.

15. The method according to claim 1, wherein said method comprises reduction of fetal distress of the fetus.

16. The method according to claim 1, wherein said method further provides vaginal delivery of the baby.

17. The method according to claim 1, wherein said method reduces the need for operative delivery of the baby.

18. The method according to claim 17, wherein the operative delivery is caesarean section (CS).

19. The method according to claim 17, wherein the operative delivery is instrumental delivery.

20. The method according to claim 1 the method comprising administering tafoxiparin twice daily.

21. The method according to claim 1, the method comprising administering tafoxiparin three times a day.

22. The method according to claim 1, the method comprising administering tafoxiparin in a daily dose of 125 to 320 mg per day.

* * * * *